United States Patent
O'Connor et al.

(10) Patent No.: US 8,618,034 B2
(45) Date of Patent: Dec. 31, 2013

(54) CONCENTRATED SURFACTANT COMPOSITIONS AND METHODS OF PREPARATION THEREOF

(75) Inventors: Stephen Moss O'Connor, Charlotte, NC (US); Phillip Lorraine Cotrell, Salisbury, NC (US)

(73) Assignee: Innospec Limited (GB)

( * ) Notice: Subject to any disclaimer, the term of this patent is extended or adjusted under 35 U.S.C. 154(b) by 0 days.

(21) Appl. No.: 13/637,433

(22) PCT Filed: Mar. 25, 2011

(86) PCT No.: PCT/GB2011/050611
§ 371 (c)(1),
(2), (4) Date: Jan. 16, 2013

(87) PCT Pub. No.: WO2011/117651
PCT Pub. Date: Sep. 29, 2011

(65) Prior Publication Data
US 2013/0109610 A1    May 2, 2013

Related U.S. Application Data

(60) Provisional application No. 61/317,890, filed on Mar. 26, 2010.

(51) Int. Cl.
*A61K 8/44* (2006.01)
*A61K 8/46* (2006.01)

(52) U.S. Cl.
USPC ........... 510/125; 510/130; 510/156; 510/424; 510/426

(58) Field of Classification Search
None
See application file for complete search history.

(56) References Cited

U.S. PATENT DOCUMENTS

| | | |
|---|---|---|
| 5,227,086 A | 7/1993 | Kacher et al. |
| 5,372,751 A | 12/1994 | Rys-Cicciari et al. |
| 6,069,262 A | 5/2000 | Walele et al. |
| 2005/0089536 A1 | 4/2005 | Loffler et al. |
| 2008/0153730 A1 | 6/2008 | Tsaur et al. |
| 2009/0062177 A1* | 3/2009 | Tsaur ............ 510/414 |
| 2009/0062406 A1 | 3/2009 | Loeffler |
| 2010/0075881 A1 | 3/2010 | Tsaur |

FOREIGN PATENT DOCUMENTS

| | | |
|---|---|---|
| EP | 0559375 A1 | 9/1993 |
| WO | 9409763 A1 | 5/1994 |
| WO | 0021492 A2 | 4/2000 |
| WO | 2005075623 A1 | 8/2005 |
| WO | 2007003289 A1 | 1/2007 |
| WO | 2007130390 A2 | 11/2007 |
| WO | 2009063250 A2 | 5/2009 |
| WO | 2011117650 A2 | 9/2011 |

OTHER PUBLICATIONS

International Preliminary Report on Patentability dated Oct. 11, 2012 for International Application No. PCT/GB11/050611.
International Search Report and Written Opinion in International Application No. PCT/GB2011/050611 dated Sep. 4, 2012.

* cited by examiner

*Primary Examiner* — Necholus Ogden, Jr.
(74) *Attorney, Agent, or Firm* — Burns & Levinson, LLP; Janine M. Susan

(57) ABSTRACT

An aqueous composition comprising: (a) an acyl isethionate of formula (I): wherein $R^1$ is an alkyl or alkenyl group having from (7) to (21) carbon atoms and M+ a cation; and (b) an amphoteric, betaine or sultaine surfactant; wherein the weight ratio of component (a) to component (b) is more than 3:1.

$$R^1CO_2CH_2CH_2SO_3^-M^+ \quad (I)$$

10 Claims, No Drawings

CONCENTRATED SURFACTANT COMPOSITIONS AND METHODS OF PREPARATION THEREOF

CROSS-REFERENCE TO RELATED APPLICATIONS

This application is a U.S. national stage application under 35 U.S.C. 371 of co-pending International Application No. PCT/GB2011/050611 filed on Mar. 25, 2011 and entitled "COMPOSITIONS", which in turn claims priority to U.S. Provisional Patent Application No. 61/317,890 filed on Mar. 26, 2010, both of which are incorporated by reference herein in their entirety for all purposes.

The present invention relates to concentrated surfactant compositions, in particular to concentrated surfactant compositions comprising acyl isethionate surfactants.

Many personal care formulations for example shampoos, body washes, skin cleansers, shower gels and the like are prepared using blends of surfactants and conditioning agents. Formulators will typically use a concentrated surfactant compositions to prepare the personal care composition. As these final compositions are typically aqueous-based it is advantageous to provide aqueous concentrated compositions which can be diluted by formulators. It is highly desirable to provide compositions comprising high concentrations of surfactants to avoid the transportation of large volumes of water. It is also desirable that the concentrated compositions are stable under conditions of storage and transportation and that they are able to be pumped i.e. they are preferably provided in flowable form.

One class of common surfactants favored for their mild properties are acyl isethionate surfactants, for example sodium cocoyl isethionate (SCI) and sodium lauroyl isethionate (SLI). However these compounds have a very low solubility in water (approximately 0.01 wt % at 25° C.) making their incorporation in liquid formulations difficult. Often they must be heated at temperatures of up to 80° C. for extended periods. SCI and SLI are commercially available in solid forms as chips, flakes or as powders. However the powdered form is dusty and difficult to handle whereas the dissolution problems are increased when using chips or flakes. It would be highly desirable to provide liquid compositions comprising high concentrations of acyl isethionate surfactants that are easy to handle and are stable in storage.

According to a first aspect of the present invention there is provided an aqueous composition comprising:
(a) an acyl isethionate of formula (I):

$$R^1CO_2CH_2CH_2SO_3^-M^+ \quad (I)$$

wherein $R^1$ is an alkyl or alkenyl group having from 7 to 21 carbon atoms and $M^+$ is a cation; and
(b) an amphoteric, betaine or sultaine surfactant;
wherein the weight ratio of component (a) to component (b) is more than 3:1.

Preferably $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium and potassium cations, and alkaline earth metal cations, for example calcium and magnesium cations. Preferably $M^+$ represents a potassium cation, or, especially, a sodium cation.

$R^1$ may be an alkyl group or an alkenyl group. Preferably $R^1$ is an alkyl group. In some embodiments component (a) may comprise a surfactant derived from a mixture of fatty acids to form a mixture of compounds of formula (I) in which $R^1$ may be different.

$R^1$ is preferably the residue of a fatty acid. Fatty acids obtained from natural oils often include mixtures of fatty acids. For example the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include coco acid, butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behenic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof. Most preferably $R^1$ comprises the residue of lauric acid, that is a saturated fatty acid having 12 carbon atoms or the residue of mixed fatty acids derived from coconut oil.

In some embodiments component (a) comprises one or more of sodium lauroyl isethionate, sodium cocoyl isethionate and sodium oleoyl isethionate.

Most preferably the composition of the present invention comprises sodium lauroyl isethionate and/or sodium cocoyl isethionate. Sodium lauroyl isethionate is especially preferred.

Component (a) is preferably present in the composition of the present invention in an amount of at least 5 wt % preferably at least 7.5 wt %, more preferably at least 10 wt %, preferably at least 11 wt %, suitably at least 12 wt %, preferably at least 13 wt %, more preferably at least 14 wt % and most preferably at least 15 wt %.

Component (a) may be present in an amount of up to 60 wt %, preferably up to 40 wt %, suitably up to 35 wt %, preferably up to 30 wt %, more preferably up to 28 wt % and most preferably up to 25 wt %.

As mentioned above the component (a) may comprise a mixture of two or more compounds of formula (I). The above amounts refer to the total amount of all such compounds in the composition.

The skilled person will appreciate that commercial sources of compounds of formula (I) may comprise impurities and/or residual starting materials. For example commercial sources of compounds of formula (I) may comprise 0 to 30 wt % fatty acids, typically 0 to 15 wt %. above amounts refer to the actual amount of active compound of formula (I) present in the composition.

Component (b) comprises an amphoteric, betaine or sultaine surfactant.

By amphoteric surfactant we mean to include any surfactants having the ability to exhibit both positive and negative sites. Component (b) may be selected from surfactants referred to as betaines, sultaines or zwitterionic surfactants or other amphoteric surfactants, for example those based on fatty nitrogen derivates.

Suitable surfactants for use as component (b) may be selected from betaines, for example alkyl betaines, alkylamidopropyl betaines, alkylamidopropyl hydroxy sultaines, alkylamphoacetates, alkylamphodiacetates, alkylamphopropionates, alkylamphodipropionates, alkyliminodipropionates and alkyliminodiacetate.

Surfactants for use as component (b) in the compositions of the present invention may include those which have an alkyl or alkenyl group of 7 to 22 carbon atoms and comply with an overall structural formula:

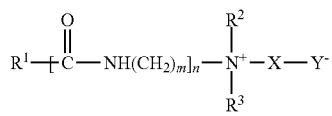

where $R^1$ is alkyl or alkenyl of 7 to 22 carbon atoms; $R^2$ and $R^3$ are each independently alkyl, hydroxyalkyl or carboxyalkyl of 1 to 6 carbon atoms; m is 2 to 4; n is 0 or 1; X is alkylene of 1 to 6 carbon atoms optionally substituted with hydroxyl; and Y is $-CO_2$ or $-SO_3$.

Surfactants suitable for use as component (b) may include simple betaines of formula:

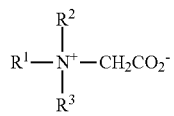

and amido betaines of formula:

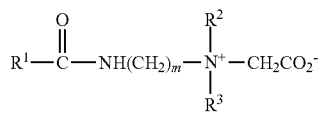

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the groups $R^1$ has 10 to 14 carbon atoms. $R^2$ and $R^3$ are preferably methyl.

Surfactant component (b) may include sultaines (or sulphobetaines) of formula:

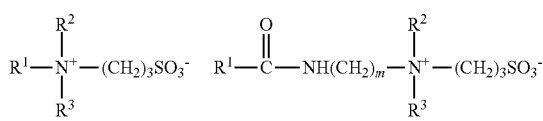

where m is 2 or 3, or variants of these in which $-(CH_2)_3SO_3^-$ is replaced by

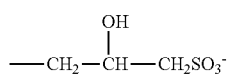

where $R^1$, $R^2$ and $R^3$ in these formulae are as defined previously.

Surfactant component (b) may include amphoacetates and diamphoacetates. Amphoacetates generally conform to the following

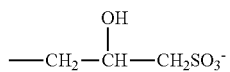

Diamphoacetates generally conform to the following formula:

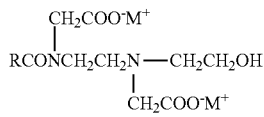

where R is an aliphatic group of 7 to 22 carbon atoms and M is a cation such as sodium, potassium, ammonium, or substituted ammonium.

Suitable acetate-based amphoteric surfactants include lauroamphoacetate; alkyl amphoacetate; cocoampho(di)acetate; cocoamphoacetate; disodium cocoamphodiacetate; sodium cocoamphoacetate; disodium cocoamphodiacetate; disodium capryloamphodiacete; disodium lauroamphoacetate; sodium lauroamphoacetate and disodium wheatgerm amphodiacetate.

Suitable betaine surfactants include alkylamido betaine; alkyl betaine, $C_{12/14}$ alkyldimethyl betaine; cocoamidopropylbetaine; tallow bis(hydroxyethyl)betaine; hexadecyldimethylbetaine; cocodimethylbetaine; alkyl amido propyl sulfo betaine; alkyl dimethyl amine betaine; coco amido propyl dimethyl betaine; alkyl amido propyl dimethyl amine betaine; cocamidopropyl betaine; lauryl betaine; laurylamidopropl betaine, coco amido betaine, lauryl amido betaine, alkyl amino betaine; alkyl amido betaine; coco betaine; lauryl betaine; diemethicone propyl PG-betaine; oleyl betaine; N-alkyldimethyl betaine; coco biguamide derivative, $C_8$ amido betaine; $C_{12}$ amido betaine; lauryl dimethyl betaine; alkylamide propyl betaine; amido betaine; alkyl betaine; cetyl betaine; oleamidopropyl betaine; isostearamidopropyl betaine; lauramidopropyl betaine; 2-alkyl-N-carboxymethyl-N-hydroxyethyl imidazolinium betaine; 2-alkyl-N-carboxyethyl-N-hydroxyethyl imidazolinium betaine; 2-alkyl-N-sodium carboxymethyl-N-carboxymethyl oxyethyl imidazolinium betaine; N-alkyl acid amidopropyl-N,N-dimethyl-N-(3-sulfopropyl)-ammonium-betaine; N-alkyl-N,N-dimethyl-N-(3-sulfopropyl)-ammonium-betaine; cocodimethyl betaine; apricotamidopropyl betaine; isostearamidopropyl betaine; myristamidopropyl betaine; palmitamidopropyl betaine; cocoamidopropyl hydroxyl sultaine; undecylenamidopropyl betaine; cocoamidosulfobetaine; alkyl amido betaine; $C_{12/18}$ alkyl amido propyl dimethyl amine betaine; lauryldimethyl betaine; ricinol amidobetaine; tallow aminobetaine.

Suitable glycinate-based amphoteric surfactants include cocoamphocarboxyglycinate; tallowamphocarboxygynicate; capryloamphocarboxyglycinate, oleoamphocarboxyglycinate, bis-2-hydroxyethyl tallow glycinate; lauryl amphoglycinate; tallow polyamphoglycinate; coco amphoglycinate; oleic polyamphoglycinate; N—$C_{10/12}$ fatty acid amidoethyl-N-(2-hydroxyethyl)-glycinate; N—$C_{12/18}$-fatty acid amidoethyl-N-(2-hydroxyethyl)glycinate; dihydroxyethyl tallow glycinate.

Preferred acetate-based amphoteric surfactants for use as component (b) include sodium lauroamphocaetate, disodium lauroamphoacetate and mixtures thereof.

Preferred betaine surfactants for use as component (b) are amido betaines. Especially preferred compounds include cocoamidopropyl betaine.

Preferred sultaine surfactants for use as component (b) include amidoalkyl hydroxy sultaines, for example cocoamidopropylhydroxy sultaine.

Preferably component (b) is selected from sultaines, betaines, glycinate-based amphoteric surfactants and mixtures thereof. More preferably component (c) is selected from sultaines, betaines and mixtures thereof. Most preferably component (c) comprises a betaine, especially an amido betaine.

Component (b), when present, is preferably present in an amount of at least 0.1 wt %, preferably at least 0.5 wt %, more preferably at least 1 wt %, for example at least 1.5 wt % or at least 2 wt %.

Component (b) may be present in an amount of up to 25 wt %, suitably up to 20 wt %, preferably up to 15 wt %, more preferably up to 10 wt %, preferably up to 8 wt %.

The weight ratio of component (a) to component (b) is more than 3:1. Preferably it is more than 3.5:1, preferably more than 4:1, for example more than 4.5:1 or more than 5:1.

The weight ratio of component (a) to component (b) may be up to 30:1, suitably up to 25:1, preferably up to 20:1, preferably up to 15:1, for example up to 10:1 or up to 8:1.

Preferably component (a) and component (b) together comprise more than 12 wt % of the composition of the first aspect of the present invention, preferably more than 14 wt %, more preferably more than 15 wt %. Suitably more than 16 wt %, preferably more than 17 wt %, for example more than 18 wt %. In some embodiments component (a) and component (b) may together comprise more than 20 wt % of the composition.

Component (a) and component (b) may together comprise up to 80 wt % of the composition of the present invention, suitably up to 60 wt %, preferably up to 55 wt %, more preferably up to 50 wt %, suitably up to 45 wt %, for example up to 40 wt %, up to 35 wt % or up to 30 wt %.

The composition of the present invention comprises component (a), component (b) and water. Preferably any further components are present in a total amount of less than 25 wt %, preferably less than 20 wt %, suitably less than 15 wt %, preferably less than 10 wt %, more preferably less than 5 wt %, preferably less than 4 wt %, less than 3 wt %, less than 2 wt % or less then 1 wt %.

The present invention provides concentrated compositions which can be used to formulate personal care compositions. These compositions are suitably in a form which enables them to be easily stored, transported and handled.

Preferably the compositions form a stable homogeneous phase at least one or more temperatures between 0° C. and 100° C., preferably at least one or more temperatures between 5° C. and 80° C., more preferably at least one or more temperatures between 10° C. and 60° C., preferably at least one or more temperatures between 15° C. and 50° C., for example at least one or more temperatures between 15° C. and 45° C.

Preferably the compositions are in a form which is flowable at least one or more temperatures between 0° C. and 100° C., preferably at least one or more temperatures between 5° C. and 80° C., preferably at least one or more temperatures between 10° C. and 60° C., preferably at least one or more temperatures between 15° C. and 50° C., for example at least one or more temperatures between 15° C. and 45° C.

The composition is suitably provided in a physically stable form. For example it does not change phase or separate into different phases on standing and is physically stable under the conditions of light, heat and pressure at which it is prepared, stored and used. For example a precipitate does not form from the composition and emulsions do not split.

The composition of the present invention is suitably a flowable composition. By flowable it is meant that the composition can be pumped or made to flow. The composition of the present invention may be any type of composition which can flow including free flowing compositions which can be easily poured and thixotropic compositions which only flow when a stress is applied.

The composition of the present invention may be provided in any suitable form. Preferably it is of substantially uniform consistency. The composition may be in the form of an emulsion. However in preferred embodiments the composition is substantially homogeneous and is present as a single phase composition.

Preferably the composition is in a stable flowable form at all temperatures of from 30 to 45° C. However embodiments which are flowable over only a narrow range, for example from 20 to 22° C. or from 30 to 32° C. are also within the scope of the invention. Such temperatures are acceptable to formulators and the compositions provide significant processing benefits compared to the use of compositions of the prior art which would have to be heated to temperatures of up to 80° C. to achieve equivalent levels of acyl isethionate.

Preferably the compositions of the present invention comprise less than 2 wt % of taurate surfactants, preferably less than 1 wt %, more preferably less than 0.5 wt %, preferably less than 0.1 wt %, preferably less than 0.05 wt %, preferably less than 0.001 wt %. In especially preferred embodiments the compositions of the present invention are substantially free of taurate surfactants. By taurate surfactants we mean to refer to compounds of formula $RCON(CH_3)CH_2CH_2SO_3M$ in which R is a linear or branched alkyl or alkenyl group and M is a counterion.

Preferably the compositions of the present invention comprise less than 2 wt % of an imidazoline amphoteric surfactant, preferably less than 1 wt %, more preferably less than 0.5 wt %, preferably less than 0.1 wt %, preferably less than 0.05 wt %, preferably less than 0.001 wt %. In especially preferred embodiments the compositions of the present invention are substantially free of imidazoline amphoteric surfactants. By imidazoline amphoteric surfactants we mean to refer to compounds having the formula:

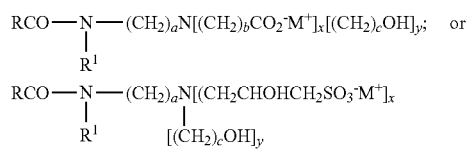

wherein a is from 1 to 3; b and c may be the same or different and are 1, 2 or 3; M is an alkali or alkaline earth metal, x is 1 or 2, y is 0 or 1 and x+y is 2; $R^1$ is H or $CH_2CH_2OH$ and R is an alkyl or alkylene radical.

Preferably the composition of the present invention comprises less than 2 wt % of alkanolamides, alkylamine oxides or mixtures thereof, preferably less than 1 wt %, more preferably less than 0.5 wt %, preferably less than 0.1 wt %, more preferably less than 0.05 wt %, preferably less than 0.01 wt %, most preferably less than 0.001 wt %. In especially preferred embodiments the compositions of the present invention are substantially free of alkanolamides and substantially free of alkylamine oxides.

According to a second aspect of the present invention there is provided a formulated personal care composition prepared from the composition of the first aspect.

According to a third aspect of the present invention there is provided a method of preparing a composition of the second aspect by diluting a composition of the first aspect. The method of the third aspect suitably involves adding one or more solvents, preferably including water to a composition of the first aspect along with optional further actives and/or excipients.

The invention will now be further described with reference to the following non-limiting example.

Example 1

Aqueous compositions were prepared having the components detailed in table 1 by adding flakes of sodium lauroyl isethionate (SLI) and cocoamido propyl betaine (CAPB) to water. The vessel was heated in a water bath at 70° C., and the mixture stirred until there were no visible solids present. The liquid was allowed to cool to room temperature and then transferred to three separate sealed vessels. These were then left at room temperature or heated to the specified test temperature 30° C. and 45° C.

Sodium lauroyl isethionate was used as a 100% non-volatile solid material comprising 78.6 wt % of the active surfactant compound and approximately 10% lauric acid.

Cocamidopropyl betaine (CAPB) was supplied as an aqueous solution containing 35 wt % non-volatile compounds and 30 wt % of the active surfactant compound.

Table 1 details the amounts of each component present in the composition as the active compound and describes the physical appearance of the composition at room temperature, 30° C. and 45° C.

TABLE 1

| Composition | SLI (wt %) | CAPB (wt %) | Appearance at: | | |
|---|---|---|---|---|---|
| | | | Room temp | 30° C. | 45° C. |
| 1 | 15.8 | 3 | Paste | Flowable Liquid | Clear flowable liquid |
| 2 | 19.7 | 3 | Paste | Flowable Liquid | Clear flowable liquid |
| 3 | 23.6 | 3 | Paste | Flowable Liquid | Clear flowable liquid |

Example 2

Aqueous compositions were prepared having the components detailed in table 2 by adding the specified components to water. The vessel was heated in a water bath at 70° C., and the mixture stirred until there were no visible solids present. The liquid was allowed to cool to room temperature and then transferred to three separate sealed vessels. These were then left at room temperature or heated to the specified test temperature 30° C. and 45° C.

Sodium lauroyl isethionate (SLI) was used as a 100% non-volatile solid material comprising 78.6 wt % of the active surfactant compound and approximately 10% lauric acid.

Sodium cocoyl isethionate (SCI) was used as a 100% non-volatile solid material comprising 84 wt % of the active surfactant compound and approximately 10% coconut acid.

Cocamidopropyl betaine (CAPB) was supplied as an aqueous solution containing 35 wt % non-volatile compounds and 30 wt % of the active surfactant compound.

Cocamidopropyl hydroxysultaine (CANS) was supplied as an aqueous solution containing 50% wt non-volatile compounds and 43% wt of the active surfactant compound.

Table 2 details the amounts of each component present in the composition as the active compound and describes the physical appearance of the composition at room temperature, 30° C. and 45° C.

TABLE 2

| SCI (wt %) | SLI (wt %) | CAPB (wt %) | CAHS (wt %) | Appearance at: | | | Viscosity in cP (at temp in ° C.) |
|---|---|---|---|---|---|---|---|
| | | | | Room temp | 30° C. | 40° C. | |
| 24.0 | | | | White solid | Unstable | Unstable | |
| | 20.0 | 3.01 | | White solid | Stable, pours | Stable, pours | 9200 (31° C.) |
| 20.0 | | 3.02 | | White solid | Stable, pours | Stable, pours | 125.6 (30.7° C.) |
| 20.0 | | | | White solid | Unstable | Unstable | |
| | 24.0 | 2.25 | | White solid | Stable, pours | Stable, pours | 5520 (32° C.) |
| 24.1 | | 2.25 | | White solid | Stable, pours | Stable, pours | 6260 (31° C.) |
| 24.0 | | | 4.31 | White solid | Stable, pours | Stable, pours | 19800 (31° C.) |

The invention claimed is:

1. An aqueous composition comprising:
(a) an acyl isethionate of formula (I):

$$R^1CO_2CH_2CH_2SO_3^-M^+ \quad (I)$$

wherein $R^1$ is an alkyl or alkenyl group having from 7 to 21 carbon atoms and $M^+$ a cation; and
(b) an amphoteric, betaine or sultaine surfactant;
wherein the weight ratio of component (a) to component (b) is more than 3:1;
wherein component (a) comprises at least 7.5 wt % of the composition;

wherein component (a) and component (b) together comprise more than 20 wt % of the composition;

wherein the composition is substantially free of taurate surfactants or comprises less than 2 wt % of taurate surfactants;

wherein the composition is substantially free of alkanolamides or comprises less than 0.1 wt % of alkanolamides;

wherein the composition is substantially free of alkylamine oxides or comprises less than 0.1 wt % of alkylamine oxides;

wherein components other than water, component (a) and component (b) not present or are present in a total amount of less than 25 wt %; and wherein the composition is a flowable composition at one or more temperatures between 15° C. and 45° C.

2. The composition according to claim 1 which comprises at least 10 wt % component (a).

3. The composition according to claim 1 wherein component (a) comprises one or more of sodium lauroyl isethionate, sodium cocoyl isethionate or sodium oleoyl isethionate.

4. The composition according to claim 1 wherein component (b) comprises an amido betaine or an amido alkyl hydroxy sultaine.

5. The composition according to claim 4 wherein component (b) comprises cocamido propyl betaine or cocamido propylhydroxy satanic.

6. The composition according to claim 1 wherein component (a) and component (b) together comprise up to 60 wt % of the composition.

7. The composition according to claim 1 which is substantially free of taurate surfactants or comprises less than 0.1 wt % of taurate surfactants.

8. A formulated personal care composition prepared from a composition as claimed in claim 1.

9. A method of preparing a personal care composition, the method comprising diluting the composition of claim 1.

10. The composition according to claim 1 which is substantially free of imidazoline amphoteric surfactants or comprises less than 0.1 wt % imidazoline amphoteric surfactants.

* * * * *

UNITED STATES PATENT AND TRADEMARK OFFICE
CERTIFICATE OF CORRECTION

| | |
|---|---|
| PATENT NO. | : 8,618,034 B2 |
| APPLICATION NO. | : 13/637433 |
| DATED | : December 31, 2013 |
| INVENTOR(S) | : Stephen Moss O'Connor et al. |

Page 1 of 1

It is certified that error appears in the above-identified patent and that said Letters Patent is hereby corrected as shown below:

In the Claims

In column 9, line 12 (claim 1), "component (b) not present" should read -- component (b) are not present --

In column 10, line 6 (claim 5), "satanic" should read -- sultaine --

Signed and Sealed this
Eleventh Day of March, 2014

Michelle K. Lee
*Deputy Director of the United States Patent and Trademark Office*